United States Patent
von Blumenthal et al.

(10) Patent No.: US 9,254,368 B2
(45) Date of Patent: Feb. 9, 2016

(54) OXYGEN REGULATION WITH AT LEAST TWO SPO₂ MONITORS AND AUTOMATIC RECOGNITION OF A SIGNAL HAVING A HIGHER RATING

(75) Inventors: Tilman von Blumenthal, Lübeck (DE); Donald Null, Bountiful, UT (US)

(73) Assignee: DRÄGERWERK AG & CO. KGaA, Lübeck (DE)

( * ) Notice: Subject to any disclaimer, the term of this patent is extended or adjusted under 35 U.S.C. 154(b) by 1061 days.

(21) Appl. No.: 13/310,195

(22) Filed: Dec. 2, 2011

(65) Prior Publication Data

US 2013/0139817 A1 Jun. 6, 2013

(51) Int. Cl.
*A61M 16/12* (2006.01)
*A61M 16/00* (2006.01)
*A61M 16/10* (2006.01)
*A61M 16/16* (2006.01)

(52) U.S. Cl.
CPC .......... *A61M 16/0051* (2013.01); *A61M 16/12* (2013.01); *A61M 16/1005* (2014.02); *A61M 16/16* (2013.01); *A61M 2016/1025* (2013.01); *A61M 2202/0208* (2013.01); *A61M 2230/06* (2013.01); *A61M 2230/205* (2013.01)

(58) Field of Classification Search
CPC ............ A61M 16/00; A61M 16/0051; A61M 16/0003; A61M 16/1005; A61M 16/1025; A61M 2205/3306; A61M 2230/06; A61M 2230/205; A61M 2230/005
See application file for complete search history.

(56) References Cited

U.S. PATENT DOCUMENTS

| | | | |
|---|---|---|---|
| 5,365,922 A | 11/1994 | Raemer | |
| 5,503,148 A * | 4/1996 | Pologe et al. | 600/323 |
| 5,865,736 A * | 2/1999 | Baker et al. | 600/323 |
| 7,290,544 B1 | 11/2007 | Sarela et al. | |
| 7,410,291 B2 | 8/2008 | Koch | |
| 2010/0139659 A1 | 6/2010 | von Blumenthal | |
| 2011/0041849 A1 * | 2/2011 | Chen et al. | 128/204.23 |

FOREIGN PATENT DOCUMENTS

DE  10 2005 037 921 B3  6/2006
DE  102009013396  8/2010

* cited by examiner

*Primary Examiner* — Valerie L Skorupa
(74) *Attorney, Agent, or Firm* — McGlew and Tuttle, P.C.

(57) ABSTRACT

A process and a device for oxygen regulation of a patient having at least two $SPO_2$ monitors and a control for automatic recognition of which measurements are more reliable. The measurement from one or more of the two $SPO_2$ is used to control the oxygen concentration delivered to a patient based on a comparison of the measurements from the at least two $SPO_2$ monitors.

20 Claims, 4 Drawing Sheets if $SPO2\_1 \geq 80 \vee SPO2\_2 \geq 80$
  Rating_1← Rating_1+ 1  if $SPO2\_1 > SPO2\_2$
  Rating_2← Rating_2+ 1  otherwise
Rating_1← Rating_1+ 1  if $|HR\_1 - HR\_ECG| < |HR\_2 - HR\_ECG|$
Rating_2← Rating_2+ 1  otherwise
SPO2_closed_loop← SPO2_1  if Rating_1> Rating_2
SPO2_closed_loop← SPO2_2  if Rating_1< Rating_2
SPO2_closed_loop← $\dfrac{SPO2\_1 + SPO2\_2}{1}$  if Rating_1= Rating_2

Fig. 3

OXYGEN REGULATION WITH AT LEAST TWO SPO₂ MONITORS AND AUTOMATIC RECOGNITION OF A SIGNAL HAVING A HIGHER RATING

FIELD OF THE INVENTION

The invention relates to oxygen regulation with at least two saturation of peripheral oxygen ($SPO_2$) monitors with an automatic selection or recognition of a signal from one of at least two $SPO_2$ monitors.

BACKGROUND OF THE INVENTION

An $SPO_2$ monitor is required for the regulation of the oxygen saturation in a patient. Physiological closed loop systems must pass over into a fallback mode in care of any error that generates an unacceptable risk. The recognition of incorrect measured $SPO_2$ values may take place by checking the signal in the $SPO_2$ itself. The manufacturer Masimo provides an index of the signal quality of an $SPO_2$ monitor. If the signal quality drops below a threshold value or the time integral of the signal quality drops below a threshold value, the control system recognizes the need for the fall back mode. However, such $SPO_2$ control systems only send a warning or alarm during phases of unacceptable signal quality such that the oxygenation of the patient can be set manually. Such $SPO_2$ control systems do not provide for the oxygenation of the patient to be set automatically.

US 20100139659 A1 relates to a device and a process for controlling a respirator with inclusion of an oxygen saturation value for compensating a device-dependent time response, a physiological time response and a measuring method-dependent time response. The device-dependent time response, the physiological time response and the measuring method-dependent time response are determined in a continuous sequence and a run time of a change in the oxygen concentration from the metering means in the respirator to the patient is determined and taken into account in regulating the oxygen concentration. The device and process would benefit greatly from increased reliability of measured $SPO_2$ values.

SUMMARY OF THE INVENTION

An object of the present invention is to increase the reliability of an $SPO_2$ control system by providing a higher correlation between the measured value essential for the control and actual oxygenation of the blood during phases of acceptable signal quality. The deviation between the actual oxygenation and the target oxygenation is reduced so that the average quality of the control is improved over long periods of time.

The present invention allows for setting the saturation of a patient's blood during phases of poor signal quality. This provides a real improvement of patient therapy as it is not always ensured that a nursing staff is immediately available in clinical practice.

Another object of the present invention is to make possible an emergency operation during phases of unacceptable signal quality to reduce the deviation between the actual oxygenation of the blood and the target oxygenation.

Yet another object of the present invention is to increase the reliability of the closed loop of the $SPO_2$ monitor. The present invention reduces the percentage of time represented by phases of unacceptable signal quality.

The control system contains at least two independent $SPO_2$ monitors. The $SPO_2$ monitors may be placed at different points or locations on a patient's body. The $SPO_2$ monitors may preferably be provided on different extremities of the patient. The system optionally has a measured value of the pulse rate or heart rate by means of an electrocardiography (ECG). Both $SPO_2$ monitors send measured values on the pulse rate or heart rate, perfusion and signal quality as well as the oxygen saturation of the patient's blood.

The trustworthiness or reliability of the measurement values is rated by automatic comparison of the measured values of the first $SPO_2$ monitor with the measurement values of the second $SPO_2$ monitor. The pulse rates or heart rates of the monitors are optionally compared with the ECG-based pulse rate. The $SPO_2$ value that is used for the next control procedure is identified from the results of the comparison. The measured $SPO_2$ signal with the higher trustworthiness or reliability is used for the control. A mean value from the two measured $SPO_2$ values is sent to the control unit in case of comparable trustworthiness or reliability of the two measured values.

In addition to the features provided in US 20100139659 A1 (the entire contents of US 20100139659 A1 are incorporated herein by reference), the system of the present invention has another $SPO_2$ monitor and an ECG. A decision unit processes a measured value, which is sent to the control unit based on the criterion discussed below.

The first criteria is the oxygen saturation level. Above or equal to 80% oxygen saturation, $SPO_2$ monitors usually indicate less than the actual saturation when poor signal quality exists. However, the probability of excessively high measured values is low. The decision unit therefore rates the higher measured value as being more trustworthy or reliable.

The second criteria is the agreement of the heart rates measured by each $SPO_2$ monitor with another reference heart rate measurement. The ECG provides a reference measurement. The $SPO_2$ monitor that has a heart rate that shows better agreement with the reference measurement is rated as being more trustworthy.

The measured values of the $SPO_2$ monitor that has proved to be better, on average, is used for controlling the oxygen concentration delivered to the patient. The mean value of the two measured values is used in case of equal values.

According to the present invention, a process for controlling a respirator is provided. A first oxygen saturation monitor is provided. A second oxygen saturation monitor is provided. A first measurement signal is detected with the first oxygen saturation monitor. The first measurement signal comprises a first patient blood oxygen saturation measurement. A second measurement signal is detected with the second oxygen saturation monitor. The second measurement signal comprises a second patient blood oxygen saturation measurement. A measuring reliability rating is determined for each of the first measurement signal and the second measurement signal when the first patient blood oxygen saturation measurement and the second patient blood oxygen saturation measurement are greater than or equal to a predetermined oxygen saturation threshold. At least one of the first measurement signal associated with the first oxygen saturation monitor and the second measurement signal associated with said second oxygen saturation monitor is selected based on the measuring reliability rating associated with each of the first measurement signal and the second measurement signal to define at least one selected measurement signal. An oxygen concentration delivered to the patient is controlled based on the at least one selected oxygen saturation measurement.

The measuring reliability rating may be determined based on at least a comparison of the first patient blood oxygen saturation measurement and the second blood oxygen saturation measurement.

The measuring reliability rating associated with one of the first measurement and the second measurement may be increased when the one of the first patient blood oxygen saturation measurement and the second patient blood oxygen saturation measurement is greater than another one of the first patient blood oxygen saturation measurement and the second patient blood oxygen saturation measurement.

The predetermined oxygen saturation threshold may be eighty percent.

An alarm element may be provided. The alarm element may be activated when the first patient blood oxygen saturation measurement and the second patient blood oxygen saturation measurement are less than the predetermined oxygen saturation threshold.

An electrocardiography device may be provided. A patient may be measured with the electrocardiography device to provide a reference heart rate. A first patient heart rate signal may be detected with the first oxygen saturation monitor. The first patient heart rate signal may comprise a first patient heart rate measurement. A second patient heart rate signal may be detected with the second oxygen saturation monitor. The second patient heart rate signal may comprise a second patient heart rate measurement. The first patient heart rate measurement may be compared with the reference heart rate measurement. The second patient heart rate measurement may be compared with the reference heart rate. The measuring reliability rating may be determined based on the comparison of the first patient heart rate measurement with the reference heart rate and the comparison of the second patient heart rate measurement with the reference heart rate.

The measuring reliability rating associated with one of the first measurement signal and the second measurement signal may be increased when a difference between the reference heart rate and at least one of the first patient heart rate measurement and the second patient heart rate measurement is less than a difference between the reference heart rate and another one of the first patient heart measurement and the second patient heart rate measurement.

The measuring reliability rating associated with the first measurement signal may be compared with the measuring reliability rating associated with the second measurement signal. The measuring reliability rating associated with the one of the first measurement signal and the second measurement signal may be greater than the measuring reliability rating associated with the another one of the first measurement signal and the second measurement signal. The at least one selected measurement signal may correspond to the one of the first measurement signal and the second measurement signal with the greater measuring reliability rating.

The measuring reliability rating associated with the first measurement signal may be compared with the measuring reliability rating associated with the second measurement signal. The at least one selected measurement signal may comprise an average of the first patient blood oxygen saturation measurement and the second patient blood oxygen saturation measurement.

An oxygen saturation bedside monitor may be provided. The oxygen saturation beside monitor may provide the second patient blood oxygen saturation measurement as output. The second patient blood oxygen saturation measurement signal may be transferred to the second oxygen saturation monitor via a network.

According to the present invention, a device for controlling a respirator is provided. The device comprises a first oxygen saturation monitor detecting a first measurement signal. The first measurement signal comprises a first patient blood oxygen saturation measurement. A second oxygen saturation monitor detects a second measurement signal. The second measurement signal comprises a second patient blood oxygen saturation measurement. A measurement selection means is provided for determining a reliability rating for each of the first measurement signal and the second measurement signal and for selecting at least one of the first measurement signal and the second measurement signal based on the measuring reliability rating associated with each of the first measurement signal and the second measurement signal when the first patient blood oxygen saturation measurement and the second patient blood oxygen saturation measurement is greater than a predetermined oxygen saturation threshold to define at least one selected measurement signal. A means is provided for controlling an oxygen concentration delivered to a patient based on said at least one selected measurement signal.

The measuring reliability rating may be determined via the measurement selection means based on at least a comparison of the first patient blood oxygen saturation measurement and the second blood oxygen saturation measurement.

The measurement selection means may increase the reliability rating associated with one of the first measurement signal and the second measurement signal when one of the first patient blood oxygen saturation measurement and the second patient blood oxygen saturation measurement is greater than another one of the first patient blood oxygen saturation measurement and the second patient blood oxygen saturation measurement.

The device may comprise an alarm device. The predetermined oxygen saturation threshold may be eighty percent. The alarm device may generate an alarm signal as output when the first oxygen saturation measurement and the second oxygen saturation measurement is less than the predetermined oxygen saturation threshold.

The device may further comprise an electrocardiography device. The electrocardiography device may provide a patient reference heart rate. The first oxygen saturation monitor may provide a first patient heart rate as output. The second oxygen saturation monitor may provide a second patient heart rate as output. The measurement selection means may receive the patient reference heart rate, the first patient heart rate and the second patient heart rate as input. The measurement selection means may determine the measuring reliability rating based on a comparison of the first patient heart rate measurement with the reference heart rate and a comparison of the second patient heart rate measurement with the reference heart rate.

The measurement selection means may increase the measuring reliability rating associated with one of the first measurement signal and the second measurement signal when a difference between the reference heart rate and at least one of the first patient heart rate measurement and the second patient heart rate measurement is less than a difference between the reference heart rate and another one of the first patient heart measurement and the second patient heart rate measurement.

The measurement selection means may select the at least one of the first measurement signal and the second measurement signal based on a comparison of the measuring reliability rating associated with the first measurement signal with the measuring reliability rating associated with the second measurement signal. The measuring reliability rating associated with the one of the first measurement signal and the second measurement signal may be greater than the measuring reliability rating associated with the another one of the first measurement signal and the second measurement signal. The at least one selected measurement signal may correspond to the one of the first measurement signal and the second measurement signal with the greater measuring reliability rating.

The measurement selection means may select the at least one of the first measurement signal and the second measurement signal based on a comparison of the measuring reliability rating associated with the first measurement signal with the measuring reliability rating associated the second measurement signal. The at least one selected measurement signal may comprise an average of the first patient blood oxygen saturation measurement and the second patient blood oxygen saturation measurement.

The device may comprise an oxygen saturation bedside monitor that provides the second patient blood oxygen saturation measurement as output. The second patient blood oxygen saturation measurement signal may be transferred to the second oxygen saturation monitor via a network.

According to the present invention, a process is provided for controlling a respirator. The process comprises providing a first measuring device. The first measuring device provides a first measurement signal as output. The first measurement signal comprises a first patient oxygen saturation measurement. A first oxygen saturation monitor is provided and the first oxygen saturation monitor receives the first measurement signal. A second measuring device is provided. The second measuring device provides a second measurement signal as output. The second measurement signal comprises a second patient oxygen saturation measurement. A second oxygen saturation monitor receives the second measurement signal. The first patient oxygen saturation measurement and the second patient oxygen saturation measurement are compared with a predetermined saturation threshold. At least one measuring reliability rating criteria is provided. The at least one measuring reliability rating criteria comprises at least a comparison of the first patient oxygen saturation measurement with the second patient oxygen saturation measurement. At least one of the first measurement signal and the second measurement signal is selected based on the at least one measuring reliability rating criteria when the first patient oxygen saturation measurement and the second patient oxygen saturation measurement are greater than or equal to the predetermined saturation threshold to define at least one selected measurement signal. An oxygen concentration delivered to the patient is controlled based on the selected one of the first measurement signal and the second measurement signal. The selected one of the first measurement signal and the second measurement signal comprises one of the first patient oxygen saturation measurement, the second patient oxygen saturation measurement and an average of the first patient oxygen saturation measurement and the second patient oxygen saturation measurement.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a view showing an algorithm used to determine which measurement from one or more of the SPO₂ monitors should be used to control the concentration of oxygen supplied to a patient.

DESCRIPTION OF THE PREFERRED EMBODIMENTS

Figure 1:
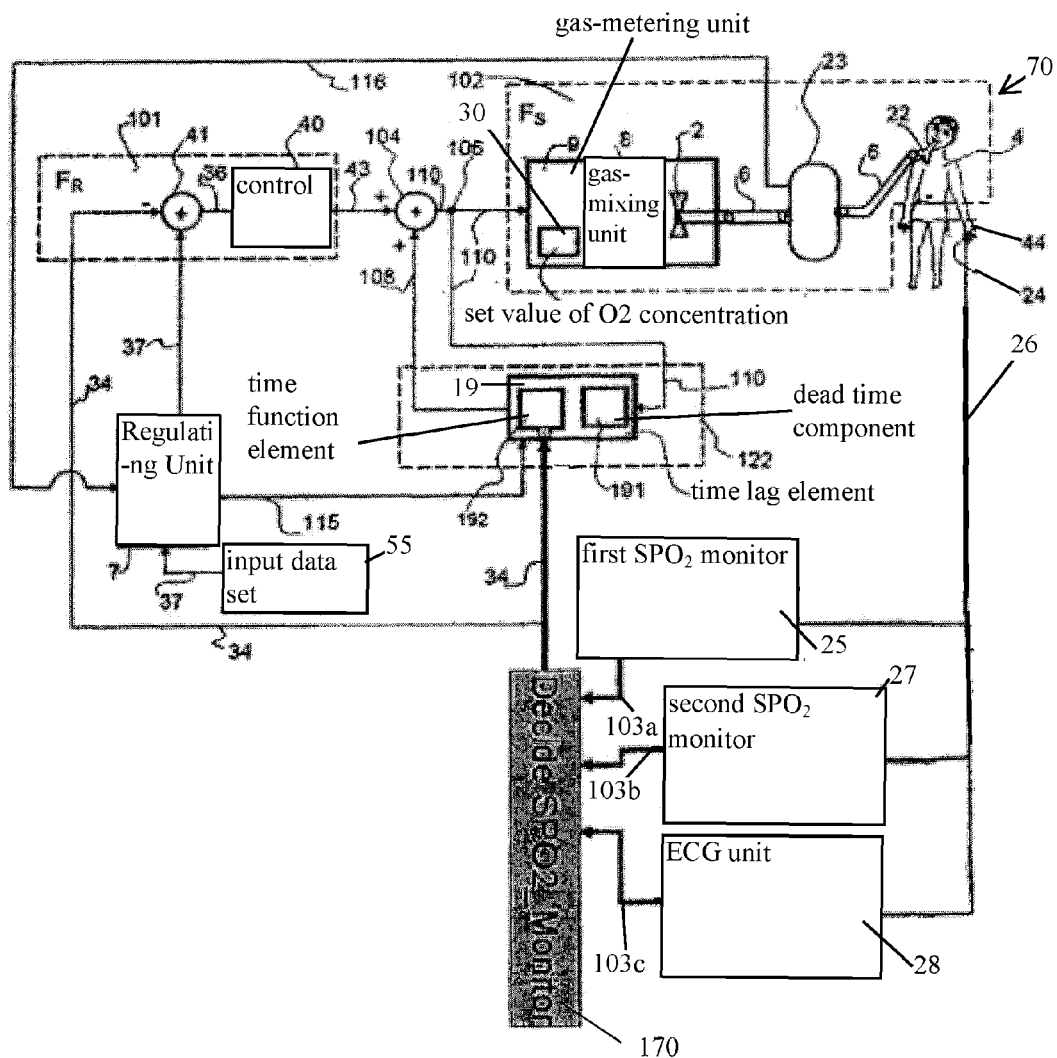
FIG. 1 is schematic view of a closed control loop.

Referring to the drawings in particular, FIG. 1 is a schematic view of a closed control loop with a first oxygen saturation-measuring means 25, a second oxygen saturation-measuring means 27, a patient 4, an ECG unit 28, a decision unit 170, a pneumatic patient connection to the respirator and time function elements formed by models.

The closed control loop 70 comprises a controller element 101, a controlled system 102, a time modeling component 122 and measuring components 25, 27, 28. Furthermore, a first summation point 104 and a first branching point 106 are arranged in series with controller 40. The control loop 70 is preferably designed as a part of the control and regulating unit 7, and controller 40 is designed in the digital form in another preferred manner.

An input data set 55 transmitted by an input unit with a set point 37 of the oxygen saturation is sent as a command variable to the controller 40 via the control and regulating unit 7. Device parameters of the respirator, of a gas path 6 and of the humidifier 23 are made available by the control and regulating unit 7 by means of a data connection 116. In addition, measured parameters of the measuring arrangement comprising the SPO₂ monitor 25 and SPO₂ monitor 27 are made available to decision unit 170. The humidifying unit 23 is in connection with the control unit 7 via the data connection 116. A state of the liquid feed to the humidifying unit 23 or of a filling level of the liquid reservoir of the humidifying unit 23 can be transmitted to the control unit 7 via the data connection 116. Control unit 7 can thereupon correspondingly adjust the device parameters and make them available to the modeling component 122 by means of the data connection 115.

The controlled system 102 comprises a patient 4, the humidifying unit 23, a gas-metering unit 9, a gas-mixing unit 8, an inspiration valve 2, a breathing tube system as the gas path 6 and a Y-piece 22 for connecting the breathing tube system 6 to the patient 4.

Figure 2:
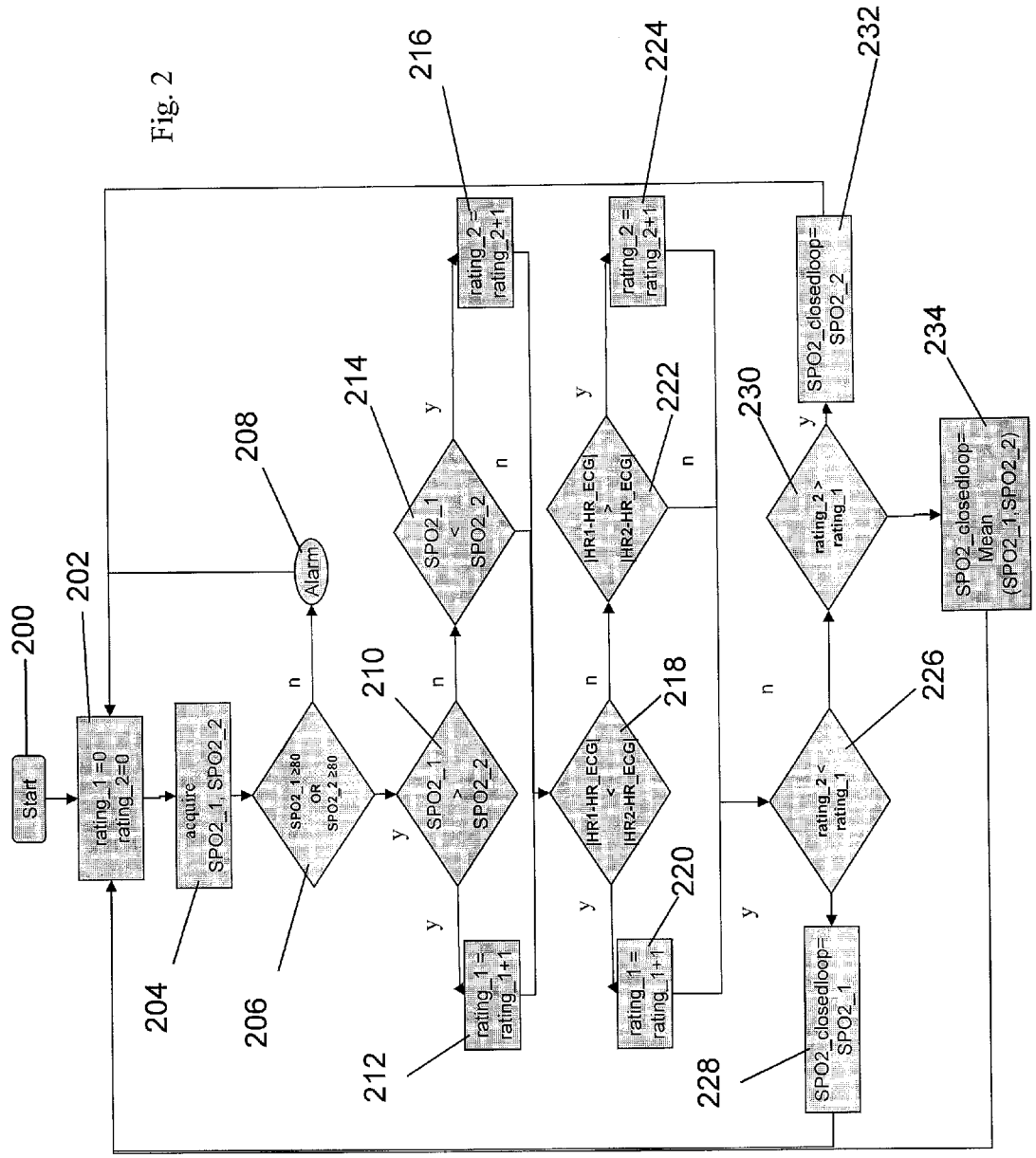
FIG. 2 is a diagram of the steps taken to determine which measurement from one or more of the SPO₂ monitors should be used to control the concentration of oxygen supplied to a patient.
Figure 4:
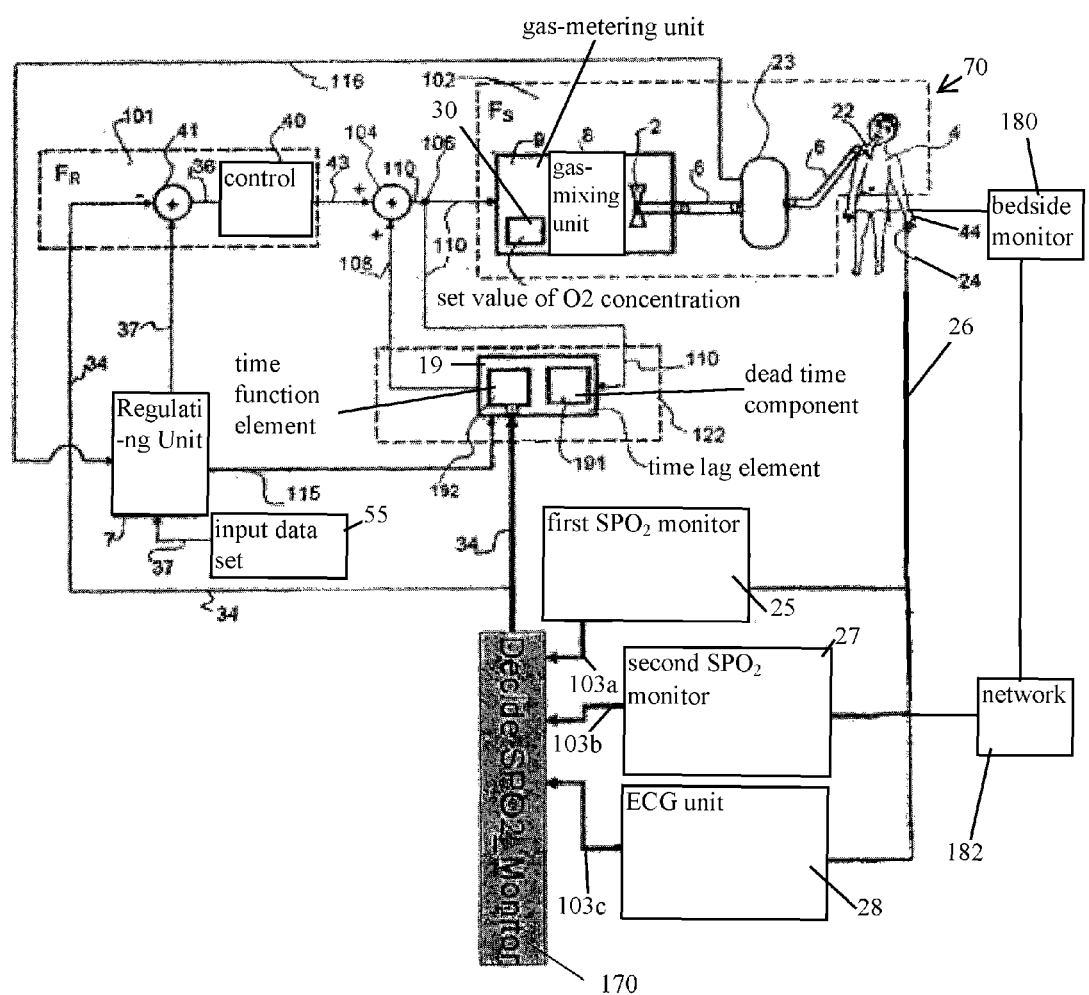
FIG. 4 is a schematic view of another embodiment of the closed control loop.

The first SPO₂ monitor 25 provides a first SPO₂ measurement 103a as output. The second SPO₂ monitor 27 provides a second SPO₂ measurement 103b as output. The first SPO₂ monitor 25 may detect the first SPO₂ measurement 103a via an SPO₂ sensor 24 at one location, such as the finger 44 of patient 4, with a sensor line 26. The second SPO₂ 27 may detect the second SPO₂ measurement 103b via an SPO₂ sensor at another location of the patient 4. Alternatively, a signal comprising the SPO₂ measurement may be also be transferred to at least one of the SPO₂ monitors from a bedside monitor 180 via a network 182, which may be wirelessly connected to at least one of the SPO₂ monitors as shown in FIG. 4. A reference patient heart rate 103c is provided as output by ECG unit 27. The first SPO₂ measurement 103a, the second SPO₂ measurement 103b and the patient heart rate 103c are provided as input to the decision unit 170. The decision unit 170 determines whether the first SPO₂ measurement 103a, the second SPO₂ measurement 103b or an average of the first SPO₂ measurement 103a and the second SPO₂ measurement 103b should be provided as an output signal based on criterion disclosed in the diagram or flow chart as shown in FIG. 2. The output signal of the decision unit 170 is sent as a controlled variable as a set of measured values of the oxygen saturation 34 to the controller input 41 of controller 40 in the controller element 101. Controller element 101 comprises a controller 40, a controller input 41, which is designed to form a difference value of the oxygen saturation 36 from the set point 37 and actual oxygen saturation value 34, and the controller output 43, which receives the difference value 36 and at which the response of the controller 40 is present corresponding to the control characteristic. One or more values of oxygen saturation 34 are also provided as input to the modeling component 122 via the decision unit 170. The modeling component 122 includes a time lag element 19. The time lag element 19 includes a first-order time function element 191 and a dead time component 192. The controller output signal 43 and feedback signal 108 of the modeling component 122 are sent to the first summation point 104. The feedback signal 108 of the modeling component 122 is likewise sent to the first summation point 104. A first branching point 106 from which the summation signal 110 is sent to the gas-metering unit 9, on the one hand, and additionally to the modeling component 122 as an input variable, is arranged in series with the first summation point 104. The set value of the oxygen concentration 30 is corrected in the gas-metering unit 9 on the basis of the summation signal 110.

FIG. 2 shows a flow chart of the steps taken by the decision unit 170 to determine the reliability rating of one or more measurements 103a associated with the first $SPO_2$ monitor 25 and the reliability rating of one or more measurements 103b associated with the second $SPO_2$ monitor 27. The decision unit 170 is initiated in step 200. The reliability ratings are set to zero in step 202. The decision unit 170 acquires at least one oxygen saturation measurement associated with the first $SPO_2$ monitor 25 and at least one oxygen saturation measurement associated with the second $SPO_2$ monitor 27 in step 204. The decision unit 170 determines whether the at least one oxygen saturation measurement associated with the first $SPO_2$ monitor 25 and the at least one oxygen saturation measurement associated with the second $SPO_2$ monitor 27 are greater than or equal to an oxygen concentration of 80%. If the oxygen saturation measurement associated with the first $SPO_2$ monitor 25 and the oxygen saturation measurement associated with the second $SPO_2$ monitor 27 are not greater than or equal to 80%, an alarm 208 is generated. The alarm 208 is of a therapeutical nature and alerts medical staff as to a dangerous level of patient oxygen saturation.

The decision unit 170 compares the oxygen saturation measurement associated with the first $SPO_2$ monitor 25 with the oxygen saturation measurement associated with the second $SPO_2$ monitor 27. The $SPO_2$ monitor with the greater oxygen saturation measurement is determined by the decision unit 170 to correspond to a more reliable measurement reading. If the oxygen saturation measurement associated with the first $SPO_2$ monitor 25 and the oxygen saturation measurement associated with the second $SPO_2$ monitor 27 are greater than or equal to 80%, the oxygen saturation measurement associated with the first $SPO_2$ monitor 25 is compared with the oxygen saturation measurement associated with the second $SPO_2$ monitor 27 to determine which of the oxygen saturation measurements is greater in step 210. If the oxygen saturation measurement associated with the first $SPO_2$ monitor 25 is greater than the oxygen saturation measurement associated with the $SPO_2$ monitor 27, the measuring reliability rating associated with the oxygen saturation measurement associated with the first $SPO_2$ monitor 25 is increased in step 212. If the oxygen saturation measurement associated with the first $SPO_2$ monitor 25 is not greater than the oxygen saturation measurement associated with the second $SPO_2$ monitor 27, the decision unit 170 checks to determine if the oxygen saturation measurement associated with the second $SPO_2$ monitor 27 is greater than the oxygen saturation measurement associated with the first $SPO_2$ monitor 25 in step 214. The measuring reliability rating associated with the oxygen saturation measurement associated with the second $SPO_2$ monitor 27 is increased in step 216 if the oxygen saturation measurement associated with the second $SPO_2$ monitor 27 is greater than the oxygen saturation measurement associated with the first $SPO_2$ monitor 25.

After comparing the oxygen saturation measurements to determine which oxygen saturation measurement is greater and providing the higher reliability rating to the greater of the two oxygen saturation measurements or determining that one $SPO_2$ measurement is not greater than the other $SPO_2$ measurement, the decision unit 170 compares the pulse rate or heart rate associated with each $SPO_2$ monitor with a reference heart rate or pulse rate, which is measured by ECG unit 28, in step 218. If the heart rate or pulse rate measurement associated with the first $SPO_2$ monitor 25 is closer to the reference heart rate or pulse rate measurement than the heart rate or pulse rate measurement associated with the second $SPO_2$ monitor 27, then reliability rating associated with the at least one measurement associated with the first $SPO_2$ monitor 25 is increased in step 220. If the heart rate or pulse rate measurement associated with the first $SPO_2$ monitor 25 is not in agreement with the reference heart rate or pulse rate or closer to the reference heart rate or pulse rate measurement in step 218 than the heart rate or pulse rate associated with the second $SPO_2$ monitor, the decision unit 170 determines whether the heart rate or pulse rate measurement associated with the second $SPO_2$ monitor 27 is closer or more in agreement with the reference heart rate or pulse rate measurement than the heart rate or pulse rate measurement associated with the first $SPO_2$ monitor 25 in step 222. If the heart rate or pulse rate measurement of the second $SPO_2$ monitor 27 is closer or more in agreement with the reference heart rate or pulse rate measurement than the heart rate or pulse rate measurement associated with the first $SPO_2$ monitor 25, the measuring reliability rating associated with the at least one measurement associated with the second $SPO_2$ monitor 27 is increased in step 224.

The decision unit 170 determines whether one or more of the at least one measurement associated with the first $SPO_2$ monitor 25 and the at least one measurement associated with the second $SPO_2$ monitor 27 should be selected based on one or more of the reliability ratings determined in steps 212, 216, 220 and 224. Steps 212 and 216 determine that the higher oxygen saturation measurement is the more reliable measurement and steps 220 and 224 qualify the $SPO_2$ sensor providing a heart rate or pulse rate as output that is closer to the reference heart rate or pulse as the more reliable $SPO_2$ sensor. If one $SPO_2$ monitor and the measurements provided as output from the respective $SPO_2$ monitor receive more votings or weight based on the ratings 212, 216, 220 and 224, the sensor signal associated with the $SPO_2$ monitor with the most votings or weight is used as a controlled variable that is provided as input to the controller input 41 of the controller element 101 and to the time modeling component 122. Examples of an $SPO_2$ monitor receiving a greater amount of reliability ratings than another $SPO_2$ monitor occurs when an oxygen saturation measurement associated with a first $SPO_2$ is greater than the oxygen saturation measurement associated with a second $SPO_2$ monitor and a heart rate or pulse rate associated with the first $SPO_2$ monitor is closer to the reference heart rate or pulse rate than the pulse rate or heart rate associated with the second $SPO_2$ monitor. If both sensors have the same amount of reliability ratings, an average of the at least one oxygen saturation measurement associated with the first SPO₂ monitor 25 and the second SPO₂ monitor 27 is used as a controlled variable as input to the controller input 41 of the controller element 101 and to the time modeling component 122. An example in which the amount of the reliability ratings of each SPO₂ monitor are the same is in a case in which the oxygen saturation measurement associated with each SPO₂ monitor is not greater than the other and the pulse rate or heart rate associated with each SPO₂ monitor is equally close to the reference pulse rate or heart rate. Another example of when the average of the at least one oxygen saturation measurement associated with the first SPO₂ monitor 25 and the second SPO₂ monitor 27 would be used is in a case in which the saturation oxygen measurement associated with one of the SPO₂ monitors is greater than the saturation oxygen measurement associated with the other one of the SPO₂ monitors and the heart rate or pulse rate associated with the other one of the SPO₂ monitors is closer to the reference heart rate or pulse rate than the heart rate or pulse rate associated with the one of the SPO₂ monitors.

The decision unit 170 determines in step 226 whether the reliability rating associated with the first SPO₂ monitor 25 is greater than the reliability rating associated with the second SPO₂ monitor 27. The at least one measurement associated with the first SPO₂ monitor 25 is selected in step 228 if the reliability rating associated with the first SPO₂ monitor 25 is greater than the reliability rating associated with the second SPO₂ monitor 27 such that the at least one measurement associated with the first SPO₂ monitor 25 is sent as a controlled variable to the controller input 41 of controller 40 in the controller element 101 and to the time modeling component 122.

If the reliability rating associated with the first SPO₂ monitor 25 is not greater than the reliability rating associated with the second SPO₂ monitor 27 in step 226, the decision unit 170 determines whether the reliability rating associated with the second SPO₂ monitor 27 is greater than the reliability rating associated with the first SPO₂ monitor 25 in step 230. The at least one measurement associated with the second SPO₂ monitor 27 is selected in step 232 if the reliability rating associated with the second SPO₂ monitor 27 is greater than the reliability rating associated with the first SPO₂ monitor 25 such that the at least one oxygen saturation measurement associated with the second SPO₂ monitor 27 is sent as a controlled variable to the controller input 41 of controller 40 in the controller element 101 and to the time modeling component 122.

An average of the at least one measurement associated with the first SPO₂ monitor 25 and the at least one measurement associated with the second SPO₂ monitor 27 is selected in step 234 if the reliability rating associated with the first SPO₂ monitor 25 is comparable or substantially equal to the reliability rating associated with the second SPO₂ monitor 27. The average of the at least one measurement associated with the first SPO₂ monitor 25 and the at least one measurement associated with the second SPO₂ monitor 27 is sent as a controlled variable to the controller input 41 of controller 40 in the controller element 101 and to the time modeling component 122. The measurements associated with the first SPO₂ monitor 25 and the second SPO₂ monitor 27 are continuously compared to each other and each respective pulse rate or heart rate associated with one of the SPO₂ monitors 25, 27 is continuously compared to the reference heart rate or pulse rate to determine which of the oxygen saturation measurements are more reliable. In one embodiment, the decision about which SPO₂ sensor is more reliable may be done in a specific period of time, such as every second.

FIG. 3 is a view showing an algorithm used to determine which oxygen saturation measurement from one or more of the SPO₂ monitors should be used to control the concentration of oxygen supplied to a patient. The algorithm shows the steps taken when the oxygen saturation measurement associated with the first SPO₂ monitor and the oxygen saturation measurement associated with the second SPO₂ monitor are greater than or equal to 80%, which are essentially the same as the steps shown in FIG. 2.

FIG. 4 is a schematic view of another embodiment of the closed control loop. The closed control loop is identical to the closed control loop shown in FIG. 1, except that one or more of the signals comprising the SPO₂ measurement is transferred to one or more of the SPO₂ monitors from a bedside monitor 180 via a network 182. The network 182 may be wirelessly connected to one or more of the SPO₂ monitors.

While specific embodiments of the invention have been shown and described in detail to illustrate the application of the principles of the invention, it will be understood that the invention may be embodied otherwise without departing from such principles.

What is claimed is:

1. A process for controlling a respirator, the process comprising the steps of:
   providing a first oxygen saturation monitor;
   providing a second oxygen saturation monitor;
   detecting a first measurement signal with said first oxygen saturation monitor, said first measurement signal comprising a first patient blood oxygen saturation measurement;
   detecting a second measurement signal with said second oxygen saturation monitor, said second measurement signal comprising a second patient blood oxygen saturation measurement;
   determining a measuring reliability rating for each of said first measurement signal and said second measurement signal when said first patient blood oxygen saturation measurement and said second patient blood oxygen saturation measurement are greater than or equal to a predetermined oxygen saturation threshold;
   comparing the measuring reliability rating associated with said first measurement signal with the measuring reliability rating associated with said second measurement signal when said first patient blood oxygen saturation measurement and said second patient blood oxygen saturation measurement are greater than or equal to the predetermined oxygen saturation threshold to provide a comparison of measuring reliability ratings;
   selecting at least one of said first measurement signal associated with said first oxygen saturation monitor and said second measurement signal associated with said second oxygen saturation monitor based on said comparison of measuring reliability ratings to define at least one selected measurement signal;
   controlling an oxygen concentration delivered to the patient based on said at least one selected oxygen saturation measurement.

2. A process in accordance with claim 1, wherein said measuring reliability rating is determined based on at least a comparison of said first patient blood oxygen saturation measurement and said second blood oxygen saturation measurement.

3. A process in accordance with claim 2, wherein said measuring reliability rating associated with one of said first measurement and said second measurement is increased when said one of said first patient blood oxygen saturation measurement and said second patient blood oxygen saturation measurement is greater than another one of said first patient blood oxygen saturation measurement and said second patient blood oxygen saturation measurement.

4. A process in accordance with claim 3, further comprising:
providing an electrocardiography device;
measuring the patient with said electrocardiography device to provide a reference heart rate;
detecting a first patient heart rate signal with said first oxygen saturation monitor, said first patient heart rate signal comprising a first patient heart rate measurement;
detecting a second patient heart rate signal with said second oxygen saturation monitor, said second patient heart rate signal comprising a second patient heart rate measurement;
comparing said first patient heart rate measurement with said reference heart rate measurement;
comparing said second patient heart rate measurement with said reference heart rate, wherein said measuring reliability rating is determined based on said comparison of said first patient heart rate measurement with said reference heart rate and said comparison of said second patient heart rate measurement with said reference heart rate.

5. A process in accordance with claim 4, wherein said measuring reliability rating associated with one of said first measurement signal and said second measurement signal is increased when a difference between said reference heart rate and at least one of said first patient heart rate measurement and said second patient heart rate measurement is less than a difference between said reference heart rate and another one of said first patient heart measurement and said second patient heart rate measurement.

6. A process in accordance with claim 4, wherein said measuring reliability rating associated with said one of said first measurement signal and said second measurement signal is greater than said measuring reliability rating associated with said another one of said first measurement signal and said second measurement signal, said at least one selected measurement signal corresponding to said one of said first measurement signal and said second measurement signal with said greater measuring reliability rating.

7. A process in accordance with claim 4, wherein said at least one selected measurement signal comprises an average of said first patient blood oxygen saturation measurement and said second patient blood oxygen saturation measurement.

8. A process in accordance with claim 1, wherein said predetermined oxygen saturation threshold is eighty percent.

9. A process in accordance with claim 8, further comprising:
providing an alarm element;
activating said alarm element when said first patient blood oxygen saturation measurement and said second patient blood oxygen saturation measurement are less than said predetermined oxygen saturation threshold.

10. A process in accordance with claim 1, further comprising:
providing an oxygen saturation bedside monitor, said oxygen saturation bedside monitor providing said second patient blood oxygen saturation measurement as output; and
transferring said second patient blood oxygen saturation measurement signal to said second oxygen saturation monitor via a network.

11. A device for controlling a respirator, the device comprising:

a first oxygen saturation monitor detecting a first measurement signal, said first measurement signal comprising a first patient blood oxygen saturation measurement;
a second oxygen saturation monitor detecting a second measurement signal, said second measurement signal comprising a second patient blood oxygen saturation measurement;
a measurement selection means for determining a reliability rating for each of said first measurement signal and said second measurement signal and for comparing said reliability rating of said first measurement signal with said reliability rating of said second measurement signal when said first patient blood oxygen saturation measurement and said second patient blood oxygen saturation measurement is greater than a predetermined oxygen saturation threshold and for selecting at least one of said first measurement signal and said second measurement signal based on said comparison of said measuring reliability rating associated with said first measurement signal and said measuring reliability rating associated with said second measurement signal when said first patient blood oxygen saturation measurement and said second patient blood oxygen saturation measurement is greater than said predetermined oxygen saturation threshold to define at least one selected measurement signal;
a means for controlling an oxygen concentration delivered to a patient based on said at least one selected measurement signal.

12. A device in accordance with claim 11, wherein said measuring reliability rating is determined via said measurement selection means based on at least a comparison of said first patient blood oxygen saturation measurement and said second blood oxygen saturation measurement.

13. A device in accordance with claim 12, wherein said measurement selection means increases said reliability rating associated with one of said first measurement signal and said second measurement signal when one of said first patient blood oxygen saturation measurement and said second patient blood oxygen saturation measurement is greater than another one of said first patient blood oxygen saturation measurement and said second patient blood oxygen saturation measurement.

14. A device in accordance with claim 13, further comprising:
an electrocardiography device, said electrocardiography device providing a patient reference heart rate as output, said measurement selection means receiving said patient reference heart rate as input, said first oxygen saturation monitor providing a first patient heart rate as output, said second oxygen saturation monitor providing a second patient heart rate as output, said measurement selection means receiving said first patient heart rate and said second patient heart rate as input, wherein said measurement selection means determines said measuring reliability rating based on a comparison of said first patient heart rate measurement with said reference heart rate and a comparison of said second patient heart rate measurement with said reference heart rate.

15. A device in accordance with claim 14, wherein said measurement selection means increases said measuring reliability rating associated with one of said first measurement signal and said second measurement signal when a difference between said reference heart rate and at least one of said first patient heart rate measurement and said second patient heart rate measurement is less than a difference between said reference heart rate and another one of said first patient heart measurement and said second patient heart rate measurement.

16. A device in accordance with claim 14, wherein said measuring reliability rating associated with said one of said first measurement signal and said second measurement signal is greater than said measuring reliability rating associated with said another one of said first measurement signal and said second measurement signal, said at least one selected measurement signal corresponding to said one of said first measurement signal and said second measurement signal with said greater measuring reliability rating.

17. A device in accordance with claim 14, wherein said at least one selected measurement signal comprises an average of said first patient blood oxygen saturation measurement and said second patient blood oxygen saturation measurement.

18. A device in accordance with claim 11, further comprising:
   an alarm device, wherein said predetermined oxygen saturation threshold is eighty percent, said alarm device generating an alarm signal as output when said first oxygen saturation measurement and said second oxygen saturation measurement is less than said predetermined oxygen saturation threshold.

19. A device in accordance with claim 11, further comprising:
   an oxygen saturation bedside monitor providing said second patient blood oxygen saturation measurement as output, said second patient blood oxygen saturation measurement signal being transferred to said second oxygen saturation monitor via a network.

20. A process for controlling a respirator, the process comprising the steps of:
   providing a first measuring device, said first measuring device providing a first measurement signal as output, said first measurement signal comprising a first patient oxygen saturation measurement;
   providing a first oxygen saturation monitor receiving said first measurement signal;
   providing a second measuring device, said second measuring device providing a second measurement signal as output, said second measurement signal comprising a second patient oxygen saturation measurement;
   providing a second oxygen saturation monitor receiving said second measurement signal;
   comparing said first patient oxygen saturation measurement and said second patient oxygen saturation measurement with a predetermined saturation threshold;
   providing at least one measuring reliability rating criteria, said at least one measuring reliability rating criteria comprising at least a comparison of said first patient oxygen saturation measurement with said second patient oxygen saturation measurement;
   determining a first measuring signal reliability rating associated with said first measurement signal when said first patient oxygen saturation measurement and said second patient oxygen saturation measurement are greater than or equal to said predetermined saturation threshold;
   determining a second measuring signal reliability rating associated with said second measurement signal when said first patient oxygen saturation measurement and said second patient oxygen saturation measurement are greater than or equal to said predetermined saturation threshold;
   comparing said first measuring signal reliability rating with said second measuring signal reliability rating to provide a comparison of measuring signal reliability ratings;
   selecting at least one of said first measurement signal and said second measurement signal based on said comparison of measuring signal reliability ratings when said first patient oxygen saturation measurement and said second patient oxygen saturation measurement are greater than or equal to said predetermined saturation threshold to define at least one selected measurement signal;
   controlling an oxygen concentration delivered to the patient based on said selected one of said first measurement signal and said second measurement signal, said selected one of said first measurement signal and said second measurement signal comprising one of said first patient oxygen saturation measurement, said second patient oxygen saturation measurement and an average of said first patient oxygen saturation measurement and said second patient oxygen saturation measurement.

* * * * *